US005366902A

United States Patent [19]

Cox et al.

[11] Patent Number: 5,366,902

[45] Date of Patent: Nov. 22, 1994

[54] COLLECTION AND DISPLAY DEVICE

[75] Inventors: Stephen J. Cox; Thomas Lydford, both of Suffolk, England

[73] Assignee: Hypoguard (UK) Limited, Suffolk, England

[21] Appl. No.: 50,168

[22] PCT Filed: Oct. 30, 1991

[86] PCT No.: PCT/GB91/01896

§ 371 Date: Jun. 22, 1993

§ 102(e) Date: Jun. 22, 1993

[87] PCT Pub. No.: WO92/07655

PCT Pub. Date: May 14, 1992

[30] Foreign Application Priority Data

Oct. 30, 1990 [GB] United Kingdom .............. 9023965.8
Nov. 8, 1990 [GB] United Kingdom .............. 9024305.6

[51] Int. Cl.[5] ........................ B01L 3/00; G01N 33/52

[52] U.S. Cl. ...................................... 436/165; 422/56; 422/57; 422/58; 422/100; 422/102; 436/169; 436/178; 436/180

[58] Field of Search ..................... 422/56, 57, 58, 100, 422/101, 102; 436/165, 169, 180, 178

[56] References Cited

U.S. PATENT DOCUMENTS

| | | | |
|---|---|---|---|
| 4,248,904 | 3/1981 | Fenimore | 427/2 |
| 4,254,083 | 3/1981 | Columbus | 422/55 |
| 4,883,760 | 11/1989 | Heelies | 435/296 |
| 4,912,034 | 3/1990 | Kalra et al. | 435/7 |
| 4,965,047 | 10/1990 | Hammond | 422/58 |
| 5,051,237 | 9/1991 | Grenner et al. | 422/56 |
| 5,100,620 | 3/1992 | Brenneman | 422/58 |
| 5,173,433 | 12/1992 | Bachard | 436/169 |
| 5,202,267 | 4/1993 | Ditlow et al. | 436/525 |
| 5,207,984 | 5/1993 | Kheiri | 422/56 |
| 5,219,525 | 6/1993 | Harrison | 422/58 |

*Primary Examiner*—Nina Bhat
*Attorney, Agent, or Firm*—Charles D. Gunter, Jr.

[57] ABSTRACT

A device and method are shown for assessing a fluid sample. The device includes a fluid receptor for receiving a sample of a fluid from an external source and a closed chamber for receiving fluid from the receptor through a fluid flow connection. Part of a wall of the chamber is provided by a member which carries a reagent which responds to a component of the fluid sample, whereby an indication of the response can be detected from the exterior of the chamber.

13 Claims, 1 Drawing Sheet

COLLECTION AND DISPLAY DEVICE

The present invention relates to a collection and display device, notably to one for receiving a sample of a fluid and for presenting that to a reagent pad integral with the sample receiving device.

BACKGROUND TO THE INVENTION

Samples of blood and other bodily fluids, for example urine, sputum etc., are frequently collected and analyzed to monitor the state of health of a human or other mammal or to identify the presence of an organism. Typically, the sample is collected in one vessel and then transferred to a separate reagent unit where a colour or other visible or non-visible indicator is developed by interaction of the sample with one or more reagents. The reagent unit or part thereof is then discarded, often with at least some of the sample still carried thereon in a state where it can contact the user and/or other parts of the test equipment. Such systems are cumbersome and carry the risk that there will be cross-infection or contamination between samples and the risk of infection of the user from the samples or the discards.

It has therefore been proposed to provide the necessary reagents in a pad upon a disposable carrier strip so that the test is carried out by applying the fluid to the reagent pad, monitoring the pad for the required colour or other change and then disposing of the pad and any remaining sample. This reduces the risk of cross-contamination between samples prior to monitoring the colour or other change in the reagent pad. However, there remains the problem of cross-contamination at the instrument where the response of the reagent is assessed, since the reagent pad and the fluid carried on it are exposed and can be contacted by the user or by exposed parts of the test apparatus.

This can be reduced by providing each patient with their own reagent response assessment unit, but this is impractical where a large number of people are being monitored at a single site, for example in a hospital. Furthermore, many people, notably the blind, infirm or very young, have difficulty in operating such a system, thus requiring that the tests on the samples of their bodily fluids be carried out by a third party. This is inconvenient and reintroduces the risk of cross-contamination, especially where such tests are carried out at a central location to reduce the costs of having to provide individual test units.

We have devised a sample collection and reagent holder system which reduces the above problems. Since the system of the invention does not expose the collected sample, as is the case with current sample reagent test strips and the like, it is possible to monitor the changes in the reagent at a central location with reduced risk of cross-infection. Due to its combined function as a sample collector and reagent holder, the system of the invention readily lends itself to use by the blind, infirm or young.

SUMMARY OF THE INVENTION

Accordingly, the present invention provides an integral fluid sample collector and sample assessment device, which device is characterised in that it comprises:

a. a fluid receptor means adapted to receive a sample of a fluid from an external source;

b. a substantially closed chamber adapted to receive fluid from the receptor means by means of fluid flow connection therebetween, the chamber having at least part of a wall thereof provided by a member carrying one or more reagents adapted to respond to one or more components of the fluid sample and adapted to give an indication of that response which can be detected from the exterior of the chamber.

Preferably, the chamber has means to vent or accommodate air displaced by the fluid entering the chamber.

Preferably, the chamber and the fluid receptor are connected by a capillary bore so that the sample is drawn by capillary action into the chamber.

Preferably, the device is in the form of a machined or moulded metal, glass or plastic unitary construction body member comprising a cup or recess having an exposed open top into which the sample to be tested is placed. The cup or recess is connected by a bore to a chamber within the body which has one face thereof formed at least in part from a demountable generally planar member which carries the reagent for the test to be carried out on or accessible from one face thereof and adapted to provide a visual display of the response from the reagent to the sample at the other face thereof. The invention is not however limited to visual display of the response. It may be possible for the response to be detected as a response outside the visible spectrum, for example in the infra-red or ultra-violet spectrum. For convenience, the invention will be described hereinafter in terms of a reagent system which develops a colour in response to contact with the bodily fluid.

The device of the invention is of especial application in testing blood samples for glucose and for convenience, it will be described with respect to this preferred use. However, it will be appreciated that the device can be used to test for one or more components in a wide range of other bodily fluids, for example blood or glucose in urine.

Preferably, the device is in the form of a generally cylindrical body having the cup or recess located at one end thereof with an axial bore leading to an axial chamber having the demountable member forming either an axial or transverse wall thereof. It is, however, preferred that the device have a diameter larger than its axial length and that the chamber have its transverse end wall remote from the axial inlet bore provided with the demountable member.

The cup or recess which is to act as the sample receptor means can be of any suitable size and shape. However, it will usually be preferred that the exposed open top to the cup or recess have an upstanding rim so that a user can present a finger carrying a drop of blood thereon to the open end and can draw the tip of the finger over the upstanding rim to aid transfer of the drop of blood from the finger tip into the cup or recess. Typically, the cup or recess will have a generally circular cross-section and will be formed by drilling or moulding an axial bore into one end of the body of the device.

The body member is provided with a bore which is to transfer the sample from the cup or recess to the chamber within the body. The bore is preferably a straight axial bore which connects the base of the cup or recess with the inlet to the chamber. Preferably, the bore is provided as a bore moulded or drilled into the body member with its axis substantially co-incident with the longitudinal axis of the body member. However, the bore may be provided by a length of a metal, for example stainless steel, capillary bore tube moulded integrally with the body member.

As indicated above, the bore is preferably a capillary bore so that the blood sample is drawn into the chamber from the cup or recess. However, the bore need not be a capillary bore and the blood sample can be caused to flow under the influence of gravity between the cup and the chamber. Thus, the bore can have a diameter of from 0.25 to 2.5 mms, notably from 0.5 to 1.5 mms. For convenience, the invention will be described hereinafter in terms of a capillary bore.

The chamber can be of any suitable shape or size and is conveniently formed during the moulding or machining of the body member so that it is a generally cylindrical chamber with its axis substantially co-incident with that of the body member. As indicated above, it is preferred that the chamber have an open end face, for example by being formed by drilling a suitable recess axially into the end face of the body member opposite to that where the sample receptor cup is located. However, the chamber can be formed with the open face as part of the side wall of the chamber.

For convenience, the invention will be described hereinafter in terms of a generally cylindrical body member having the receptor cup at one and thereof and with the open face to the chamber at the other end, the cup, capillary bore and chamber all being located with their longitudinal axes substantially co-incident, whereby the device is radially symmetrical.

The chamber receives the sample through an inlet from the capillary bore, which is preferably merely the outlet to the bore. The volume of the chamber is selected so that sufficient fluid is drawn into the chamber to activate the reagent(s) in the demountable member to the desired extent. The chamber can have an axial dimension which is sufficiently small so that the fluid entering the chamber flows by capillary action over the internal faces of the chamber and onto the inner face of the demountable member forming the fluid testing member so as to ensure uniform wetting of the member with the fluid to be tested. However, where it is necessary to employ dimensions which do not achieve this, for example due to manufacturing restrictions, it may be necessary to achieve the spreading of the fluid by "flicking" the device transversely or axially to aid transfer of the sample through the capillary bore and onto the surface of the test member.

Typically, the chamber will have a transverse diameter to axial depth ratio of from 12:1 to 5:1. It is also preferred that the axial depth of the chamber be from 0.5 to 1.5 mm to ensure adequate spread of blood or other fluid over the walls of the chamber.

Alternatively, the chamber can be dimensioned so that the fluid will form a droplet at the chamber end of the capillary bore. The droplet can then be detached to fall at an accurately known position on the test member surface forming part of the opposite wall. If required, the outlet to the capillary bore can be provided with a sharp rim to aid separation of the droplet from the bore outlet and/or the walls of the chamber adjacent the bore outlet can be given a surface coating of a material which is not readily wet by the fluid entering the chamber. For example, the internal surfaces of the chamber can be given a coating of a polytetrafluoroethylene polymer or part of the chamber walls can be formed from such a material.

By forming the chamber so that the fluid forms a droplet at the outlet to the capillary bore rather than spreading over the inner walls of the chamber, the droplet falls upon a restricted area of the chamber wall opposed to the outlet of the capillary bore rather than uniformly wetting the walls of the chamber. It is thus possible to limit the lateral spread of the droplet over the test member and to concentrate it at a given location. We have found that this enables satisfactory results to be achieved with a smaller sample than hitherto, for example to use from 30 to 70% of the sample hitherto considered necessary.

Typically, the droplets formed at the outlet to a tube have a diameter of from 1 to 5 times the internal bore of the tube outlet. Therefore, where transfer of the fluid from the capillary bore to the test member is achieved by detachment of a droplet, it is preferred that the chamber have an axial depth of from 1 to 5 mm. If required, the droplet formed at the end of the bore can be detached by rapping the device sharply, for example by flicking it with a finger or tapping it sharply onto a surface.

It will be appreciated that the axial depth of the chamber may not be sufficient, for example due to manufacturing requirements, to permit the droplet to form completely and detach from the capillary bore outlet. In such a case, the meniscus of the fluid may contact the opposed face of the test member so that the fluid then forms a bridge between the member surface and the outlet from the capillary bore. Again, it may be necessary to flick the device axially or transversely to achieve contact between the meniscus and the surface of the test member.

The chamber is preferably also provided with means whereby air displaced by the fluid as it enters the chamber can be accommodated or vented, notably where the fluid reaches the reagent pad by wetting the walls of the chamber. The walls of the chamber can be formed with a bellows or flexible section to allow the internal volume of the chamber to be increased to achieve this. However it is preferred to vent the displaced air from the chamber so as to retain a simple and substantially rigid structure for the device. Preferably, that radial wall of the chamber adjacent the fluid inlet to the chamber is provided with air vents, for example simple radial or axial bores in the chamber wall. The optimum number and size of such bores can readily be determined by simple trial and error tests. It is preferred that such air vent bores have a diameter which is sufficiently small to prevent capillary action drawing fluid into those bores.

As stated above, at least part of one wall of the chamber is provided by a test member incorporating one or more reagents to respond to one or more components in the sample being assessed. The reagents can be any of those conventionally used to test blood or other fluids and can be incorporated into the test member as a surface pad on one face of the member or can be impregnated into the material from which the member is made so that the fluid can access the reagents when it contacts the surface of the test member. The test member is one which preferably develops some visual response to the component of the fluid being assessed and this response is viewed from the outside of the chamber, for example by forming the test member as a transparent or translucent sheet carrying the reagent pad on one face thereof.

The test member can be formed as a sheet member, optionally in a suitable support frame, which is clamped or otherwise affixed to the open face of the chamber. However, it is particularly preferred to form the test member as a disc of sheet material secured to the chamber by adhesive, and to provide the reagent as a pad located generally centrally upon the internal face of that disc. The disc is applied to the end wall of the chamber which is formed with a circular aperture through which the fluid can spread to wet the inner face of the disc. The disc preferably has a blanking or opaque annular member or component so that the area of the disc visible from the outside of the chamber coincides with the area of the reagent pad on the inside of the disc. In this way the position of the area of the device of the invention to be inspected to monitor the colour or other change in the reagent pad can be accurately predicted. This aids mechanical observation of the change using optical or other means at a central processing location, rather than relying on visual inspection. Furthermore, such a construction is of especial benefit when the fluid is applied to the reagent pad as a droplet detaching from the capillary bore outlet as described above.

The device of the invention readily lends itself to manufacture as a plastic moulding to which a standard shape and form of reagent disc can be applied over the open end face of the chamber to provide a closed chamber into which the blood or other sample is drawn automatically by capillary action from the sample receptor cup. The sample is thus retained within a closed environment and the risk of cross-contamination between samples is much reduced. The sample in the device can then be assessed mechanically with reduced risk of cross-contamination at the test device, yet is simple and easy for the aged or infirm to use. Since the device can be accurately located in a suitable test device and the position of the test member fixed with respect to the test device, the device of the invention can readily be used by the blind.

DESCRIPTION OF THE PREFERRED EMBODIMENT OF THE INVENTION

Figure 1:
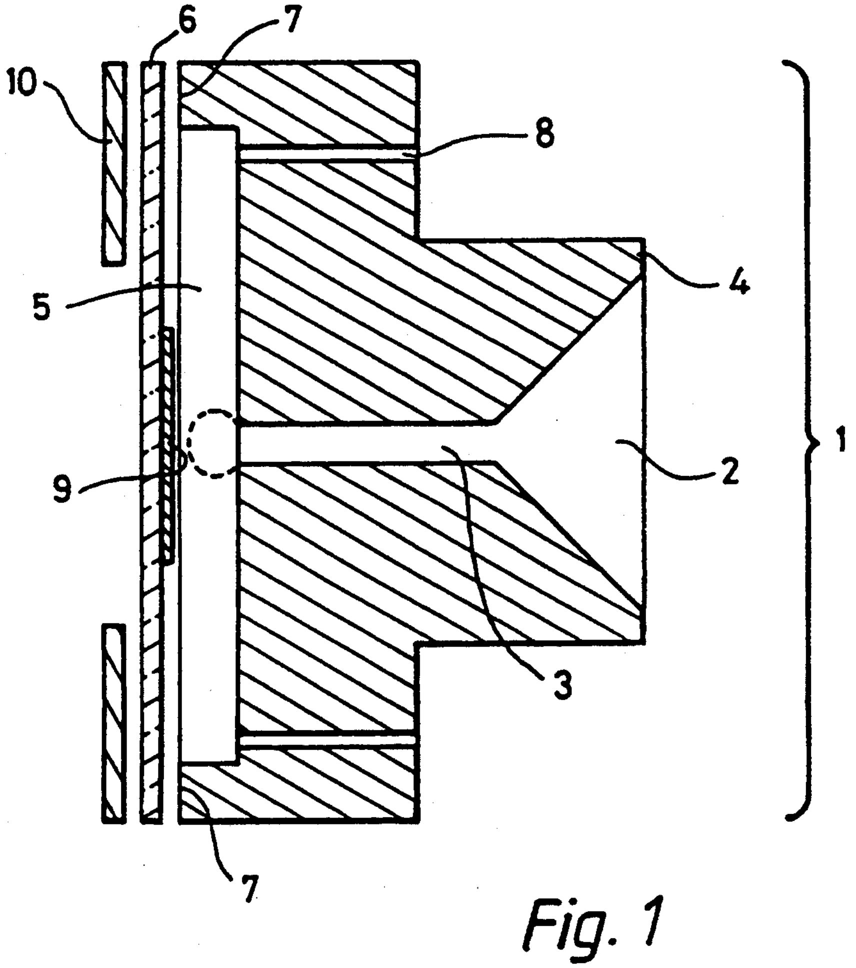
FIG. 1 is an axial cross-section through the device.
Figure 2:
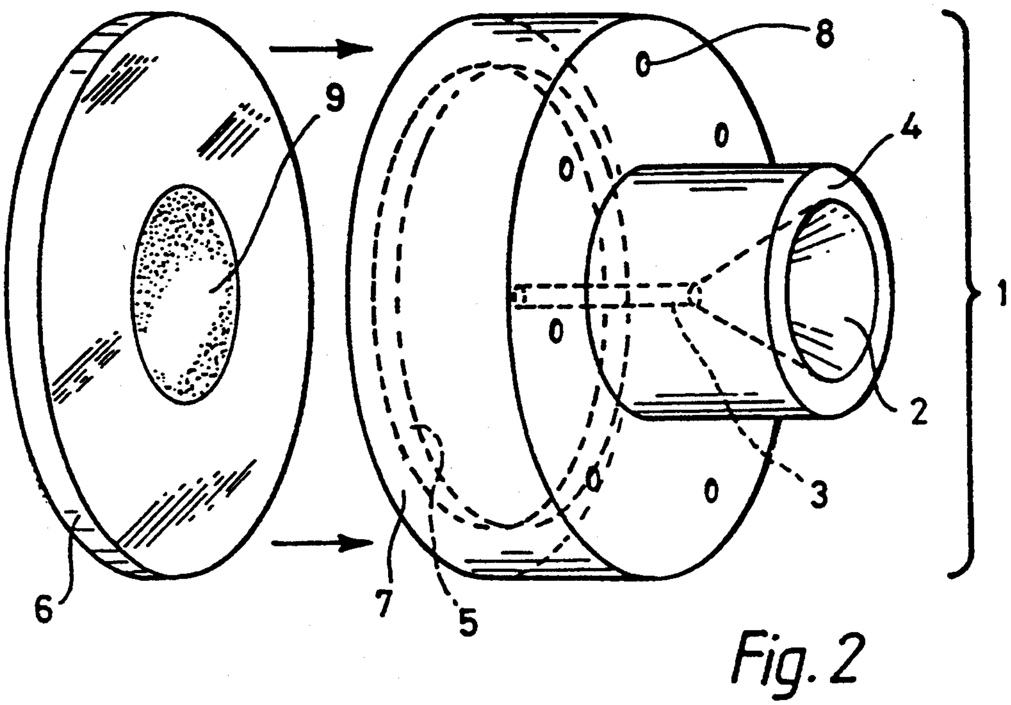
FIG. 2 is an exploded perspective view of the components of the device.

The device comprises a cylindrical housing member 1 injection moulded from a suitable plastic, for example a polystyrene; or machined from a metal such as stainless steel; or glass. At one end, the housing is formed with a sample receiving cup 2 connected to an axial capillary bore 3. The cup 2 has a rim 4 against which a user can draw his fingertip so as to transfer a drop of blood into the cup 2. Capillary bore 3 connects the base of cup 2 with the chamber 5 formed in the other end of the device. Chamber 5 has an open end face which is closed by applying an adhesive disc 6 to the annular rim 7 of the chamber. The chamber 5 is vented to the atmosphere by axial vent bores 8. Preferably, the housing, chamber, bore, cup and vent bores are formed symmetrically about the longitudinal axis of the housing.

The disc 6 carries substantially centrally thereon a reagent pad 9 and disc 6 is formed from a suitable transparent plastic so that the outer face of pad 9 can be seen through the material of the disc. A masking annular disc 10 is affixed to the outer face of disc 6 which serves both to mask the outer edge of the disc 6 and to support the central area of the disc. In an alternative form of disc 6, the reagent can be impregnated into the material of the disc and the masking rim 10 can be an integral part of the construction of the disc as opposed to being a separate component as shown.

In use, a user wipes his finger across the rim of cup 2 to transfer a drop of blood into the cup. The blood travels along capillary bore 3 due to capillary action and either spreads over the internal walls of chamber 5 to wet the reagent pad 9 or forms a droplet (shown dotted in FIG. 1) which detaches to fall directly onto the reagent pad 9. The blood sample is contained within chamber 5 and there is little risk of escape of the blood to contaminate the user, other samples or any test machine in which the response of the reagent is assessed. The reagent responds to one or more of the components in the blood in the usual manner and this response can then be observed through the circular viewing aperture in rim 10 from outside the container. Again, this response can be viewed without the need to remove the blood from chamber 5, further reducing the risk of cross-contamination.

Once the response has been generated, it can be observed and the device then discarded. Since the device is of known shape and dimensions and the location of the viewing aperture in rim 10 are accurately known, the device can readily be mounted in a suitable receptacle in a response monitoring device so that the outer face of disc 6 can be observed at the position of pad 9. The device can thus readily be handled mechanically where large numbers of samples are to be processed, or the device can be readily handled by a blind or infirm person to locate it in a monitoring device.

The invention thus also provides a method for testing a fluid sample for the presence of a component or property therein, which method is characterised in that the sample of fluid is applied to the receptor of a device as claimed in any one of the preceding claims, the fluid is allowed to flow through the bore to the chamber and to contact the reagent(s) carried by the wall thereof; and observing the response of the reagent(s) to the fluid externally through the wall of the chamber.

We claim:

1. A device for assessing a fluid sample, which device comprises:

a. a fluid receptor means for receiving a sample of a fluid from an external source, said fluid receptor means comprising a cup or recess having an exposed open top having a rim across which a user may wipe his finger so as to transfer a sample of blood from the finger into the cup or recess;

b. a substantially closed chamber adapted to receive fluid from the receptor means;

c. a bore connecting the fluid receptor means and the chamber for transferring said fluid from the receptor means to the chamber, which bore has an outlet at said chamber end of the bore;

d. a generally planar member removably mounted upon the device and providing at least part of one wall of said chamber, said member carrying one or more reagents adapted to respond to one or more components of the fluid sample and adapted to give an indication of that response which can be detected from the exterior of the chamber, said reagents being located generally centrally on said member and in register with the outlet of said bore into the chamber;

wherein the diameter of the outlet of said device is selected such that the fluid in the bore is adapted to form a droplet or meniscus at the outlet to the bore, whereby the bore is adapted to conduct the fluid from the receptor to the chamber and to deposit the fluid substantially centrally onto the reagent carrying area of the said reagent carrying member.

2. A device as claimed in claim 1, wherein the said reagent is located on or accessible from the chamber adjacent face of the said generally planar member and is adapted to provide a visual display of the response from the reagent to the sample at the other face thereof.

3. A device as claimed in claim 1, wherein the chamber is provided with means to vent or accommodate air displaced by the fluid entering the chamber.

4. A device as claimed in claim 1, wherein the chamber and the fluid receptor are connected by a capillary bore.

5. A device as claimed in claim 1, wherein it is of a generally radially symmetrical form having the fluid receptor located at one end thereof and the chamber at the other end thereof and having an axial bore for fluid flow connection between the chamber and the receptor.

6. A device as claimed in claim 1, wherein the generally planar member forms at least part of the transverse end wall of the chamber.

7. A device as claimed in claim 6, wherein the generally planar member comprises a transparent or translucent planar member having applied thereto and accessible from one face thereof the reagents to respond to the fluid sample and adapted to provide a visual response to the fluid sample through the other face of the member.

8. A device as claimed in claim 1, wherein the chamber has an internal transverse diameter to axial depth ratio which is from 12:1 to 5:1.

9. A device as claimed in claim 1, wherein the bore has a diameter of from 0.25 to 2.5 mms and the chamber has an axial depth of from 0.5 to5 mms.

10. A device as claimed in claim 1, wherein the reagent(s) respond to glucose in a blood sample.

11. A device as claimed in claim 1, wherein the said generally planar member comprises a transparent or translucent substrate adapted to be removably attached across an open end face of the chamber, the substrate carrying one or more test reagents applied thereto and carrying an annular disc of an opaque material surrounding the reagents so as to restrict the development of the response to the fluid sample to the central area of the substrate.

12. A method for testing a fluid sample for the presence of a component or property therein, wherein the sample of fluid is applied to the fluid receptor of a device as claimed in claim 1, the fluid is allowed to flow through the bore to the chamber and to form a drop or partial drop at the chamber end of the bore which contacts the reagent carrying surface of the generally planar member so as to contact the reagent(s) carried thereon; and observing the response of the reagent(s) to the fluid externally through the planar member.

13. A method as claimed in claim 12, wherein the fluid is blood and the reagents give a colour response to the glucose content of the sample.

* * * * *